(12) United States Patent
Manning et al.

(10) Patent No.: US 8,533,006 B2
(45) Date of Patent: *Sep. 10, 2013

(54) PATIENT-INTERACTIVE HEALTHCARE MANAGEMENT

(75) Inventors: Michael G. Manning, Ambler, PA (US); Martha Jean Elizabeth Minniti, Ambler, PA (US); Ian G. Rawson, Pittsburgh, PA (US)

(73) Assignee: CarePartners Plus, Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/115,801

(22) Filed: May 25, 2011

(65) Prior Publication Data
US 2011/0225006 A1   Sep. 15, 2011

Related U.S. Application Data

(63) Continuation of application No. 11/848,051, filed on Aug. 30, 2007, now Pat. No. 7,979,286.

(60) Provisional application No. 60/824,012, filed on Aug. 30, 2006, provisional application No. 60/868,013, filed on Nov. 30, 2006, provisional application No. 60/889,294, filed on Feb. 12, 2007.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ............................................................. 705/2
See application file for complete search history.

(56) References Cited

U.S. PATENT DOCUMENTS

| | | | |
|---|---|---|---|
| 4,858,121 A | 8/1989 | Barber et al. |
| 5,867,821 A | 2/1999 | Ballantyne et al. |
| 6,148,297 A | 11/2000 | Swor et al. |
| 6,151,581 A | 11/2000 | Kraftson et al. |
| 6,177,940 B1 | 1/2001 | Bond et al. |
| 6,208,873 B1 | 3/2001 | Black et al. |

(Continued)

FOREIGN PATENT DOCUMENTS
WO    WO 2008/027490    3/2008

OTHER PUBLICATIONS

Brennan, Improving Health Care by Understanding Patient Preferences: The Role of Computer Technology, Journal of the American Medical Informatics Association vol. 5 No. 3 May/Jun. 1998.*

(Continued)

*Primary Examiner* — Tran Nguyen
(74) *Attorney, Agent, or Firm* — Woodcock Washburn, LLP

(57) ABSTRACT

A patient-interactive health care management system provides means for healthcare services rendered by a physician to a patient to be confirmed by the patient immediately after the healthcare services are rendered. The patient is provided the ability to verify the accuracy of an invoice for the rendered services/goods and provide an assessment of the rendered services/goods. In an example embodiment, the patient provides this information via an information station located at the healthcare facility in which the healthcare services/goods are rendered. The information gathered from the patient is provided to the party responsible for paying for the rendered healthcare services/goods. In an example embodiment, the paying party compares the patient provided information with the invoice received from the healthcare provider to assess the accuracy of the invoice.

26 Claims, 19 Drawing Sheets

(56) References Cited

U.S. PATENT DOCUMENTS

| | | |
|---|---|---|
| 6,208,973 B1 | 3/2001 | Boyer et al. |
| 6,343,271 B1 | 1/2002 | Peterson et al. |
| 6,453,297 B1 | 9/2002 | Burks et al. |
| 6,692,436 B1 | 2/2004 | Bluth et al. |
| 6,820,058 B2 | 11/2004 | Wood et al. |
| 6,826,535 B2 | 11/2004 | Wood et al. |
| 6,826,536 B1 * | 11/2004 | Forman .............................. 705/4 |
| 6,873,960 B1 | 3/2005 | Wood et al. |
| 7,039,593 B2 | 5/2006 | Sager |
| 7,039,628 B2 | 5/2006 | Logan, Jr. |
| 7,047,204 B1 | 5/2006 | Wood et al. |
| 7,072,842 B2 | 7/2006 | Provost et al. |
| 7,979,286 B2 | 7/2011 | Manning et al. |
| 2002/0032583 A1 | 3/2002 | Joao |
| 2002/0111826 A1 | 8/2002 | Potter et al. |
| 2002/0148893 A1 | 10/2002 | Walsh et al. |
| 2003/0037065 A1 | 2/2003 | Svab |
| 2003/0083903 A1 | 5/2003 | Myers et al. |
| 2004/0078235 A1 | 4/2004 | Tallal, Jr. |
| 2005/0273363 A1 | 12/2005 | Lipscher et al. |
| 2006/0010007 A1 | 1/2006 | Denman et al. |
| 2006/0111941 A1 | 5/2006 | Blom |
| 2006/0143052 A1 | 6/2006 | Fotsch et al. |
| 2008/0059230 A1 | 3/2008 | Manning et al. |
| 2009/0055221 A1 | 2/2009 | Loftus et al. |
| 2011/0270632 A1 | 11/2011 | Manning et al. |

OTHER PUBLICATIONS

"Healthcare Review: Welcome to Health Care Reviews" http://www.healthcarereviews.com, Jan. 16, 2008, accessed Mar. 17, 2008, 1 page.

Dudley, "Managed Care in Transition: Health Policy 2001", N. Eng. J. Medicine, 344(14), Apr. 5, 2001, 6 pages.

Williams et al., "Patient use of a Computer for Prevention in Primary Care Practice", Patient Education and Counseling, Apr. 19, 1995, 25, 283-292.

Kalb, "Health Care Fraud and Abuse", The Journal of the American Medical Association:, Sep. 1999, 282(12), 1163-1168.

* cited by examiner

FIGURE 5

|  | Yes | No |
|---|---|---|
| Are You Satisfied With The Care You Received Today? | ☐ | ☐ |
| Do You Plan To Do What We Discussed? | ☐ | ☐ |
| Do You Have Any Questions? | ☐ | ☐ |

Before You Leave, Please Review 5 Things That Are Important For You To Remember

1. Good foot and eye care will decrease the chance of amputation and blindness
2. Having normal blood pressure will decrease the likelihood of heart attack, stroke, vascular or kidney problems
3. Having normal cholesterol levels will help your heart, brain and kidneys to function properly
4. Having normal Hemoglobin A1c levels will help decrease the likelihood of heart attack, vascular problems, stroke, or amputation
5. Diabetics who work with their practitioner to control their weight and blood sugar will have the best outcomes

FIGURE 12

|                                               | Yes | No |
|-----------------------------------------------|-----|-----|
| Are You Satisfied With The Care You Received Today? | ☐ | ☐ |
| Do You Plan To Do What We Discussed? | ☐ | ☐ |
| Do You Have Any Questions? | ☐ | ☐ |

Before You Leave, Please Review 5 Things That Are Important For You To Remember

1. Good foot and eye care <u>will</u> decrease the chance of amputation and blindness
2. Having normal blood pressure <u>will</u> decrease the likelihood of heart attack, stroke, vascular or kidney problems
3. Having normal cholesterol levels <u>will</u> help your heart, brain and kidneys to function properly
4. Having normal Hemoglobin A1c levels <u>will</u> help decrease the likelihood of heart attack, vascular problems, stroke, or amputation
5. Diabetics who work with their <u>practitioner</u> to control their weight and blood sugar <u>will</u> have the best outcomes

* Before you leave, please take the activity list I have prepared for you. In order to achieve the best possible health, I would like you to record, for 12 weeks, how frequently you complete the activities listed in the activity list. I wrote my name on the activity list in case you have any questions about the instructions. Please bring this activity list with you to our next visit to see what kind of progress you are making.

FIGURE 13

Good Foot Care

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Wore shoes that fit well everyday | | | | | | | | | | | | |
| ✓Dried between toes everyday | | | | | | | | | | | | |
| ✓Didn't walk bare foot | | | | | | | | | | | | |

Achieve Normal Blood Pressure

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Followed my diet instructions | | | | | | | | | | | | |
| ✓Followed my exercise instructions | | | | | | | | | | | | |
| ✓Took slow deep breaths when feeling stressed | | | | | | | | | | | | |
| ✓Took my meds as prescribed | | | | | | | | | | | | |

Achieve Normal Cholesterol

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Followed my diet instructions | | | | | | | | | | | | |
| ✓Increased my fiber intake | | | | | | | | | | | | |
| ✓Took my meds as prescribed | | | | | | | | | | | | |

Achieve Normal Hemoglobin A1c Levels

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Tracked my blood sugar daily. | | | | | | | | | | | | |
| ✓Compared my blood sugar to HA1c levels | | | | | | | | | | | | |

Good eye Care

| | Date of exam |
|---|---|
| ✓Eyes examined and dilated annually | |

FIGURE 14

Achieve Normal Blood Pressure

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Maintained healthy weight | | | | | | | | | | | | |
| ✓Followed exercise program | | | | | | | | | | | | |
| ✓Reduced stress | | | | | | | | | | | | |
| ✓Took meds as prescribed | | | | | | | | | | | | |

Understand Physician's Instructions

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Followed my plan | | | | | | | | | | | | |

Do Not Use Tobacco, Excessive Alcohol, Or Non-Prescription Drugs

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Decreased my usage | | | | | | | | | | | | |

Regular Seatbelt Use

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Used my seatbelt regularly | | | | | | | | | | | | |

Follow Your Treatment Plan

| Weekly Care checklist | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|
| ✓Followed my diet instructions | | | | | | | | | | | | |
| ✓Followed my exercise instructions | | | | | | | | | | | | |
| ✓Took my meds as prescribed | | | | | | | | | | | | |

FIGURE 15

PATIENT-INTERACTIVE HEALTHCARE MANAGEMENT

CROSS REFERENCE TO RELATED APPLICATIONS

The instant application is a continuation of U.S. patent application Ser. No. 11/848,051, entitled "PATIENT-INTERACTIVE HEALTHCARE MANAGEMENT," file Aug. 30, 2007, which is hereby incorporated by reference in its entirety. U.S. patent application Ser. No. 11/848,051 claims benefit to U.S. provisional patent application No. 60/824,012, entitled "HEALTH CARE SYSTEM," filed Aug. 30, 2006, which is hereby incorporated by reference in its entirety. U.S. patent application Ser. No. 11/848,051 also claims benefit to U.S. provisional patent application No. 60/868,013, entitled "HEALTH PROVIDER MANAGEMENT SYSTEM," filed Nov. 30, 2006, which is hereby incorporated by reference in its entirety. U.S. patent application Ser. No. 11/848,051 also claims benefit to U.S. provisional patent application No. 60/889,294, entitled "HEALTH CARE SYSTEM," filed on Feb. 12, 2007, which is herby incorporated by reference in its entirety.

TECHNICAL FIELD

The technical field generally relates to health care, and more specifically relates to healthcare management, healthcare cost analysis, financial services, and healthcare service analysis.

BACKGROUND

Healthcare costs are on the rise. This is due in part to payment for services and/or goods that were not actually provided. It is not uncommon for payment of medical service to be paid, at least in part, by a third party other than the patient (e.g., health insurance company, government provider such as Medicare or Medicaid). Often, the third party provides payment in accordance with an invoice listing the services/goods provided. On occasions, the invoice may not be accurate.

A patient typically receives, after medical services have been provided, an invoice comprising an itemized list of the services/goods. For example, when a patient visits a physician for treatment, upon completion of the visit, the patient is provided an itemized invoice which should properly itemize services rendered. At times however, the itemized services do not accurately reflect the services rendered and/or goods (e.g., medications) provided. For a variety of reasons, inaccuracies may go unnoticed and/or uncorrected. A patient may not pay attention to the invoice, for example, because the patient is not responsible for paying the entire bill. The patient may not understand the codes and/or terminology used to describe the services. Or, the patient may not look at the invoice until well after leaving the physician's office. At his point, the patient may feel it is too late to correct any inaccuracies, or not remember what services/goods were provided. Thus, it is not uncommon for an inaccurate invoice, prebill, bill, charge ticket, or the like to be submitted for payment. The lack of success to date in verifying the accuracy of invoices (e.g., by the paying party) or to correct found inaccuracies have had detrimental effects upon the cost of health care.

SUMMARY

Healthcare accountability and management are provided via patient-interactive contemporaneous evaluation and verification of provided services. Upon completion of provided services, the recipient of the services (e.g., the patient) evaluates the services and verifies the accuracy of an invoice of the services. The results thereof are submitted to the paying party along with an invoice of the services. In an example embodiment, during the evaluation process, queries and information provided to the recipient are structured to provide interventional and educational changes to patient behavior. Accordingly, the patient is aided in adapting to changing healthcare behavior and entering into a more robust relationship with a healthcare provider.

In an example configuration, information stations (e.g., kiosks, processors having Internet access, mobile devices, or the like), are located at or near facilities (e.g., out patient department, physician's offices, clinics, hospitals, nursing homes, assisted living centers, homehealth settings, hospice, dental, optical offices, mental health institutions, rehab, occupational healthsettings, retail healthcare settings, or the like) wherein the services are provided. Upon completion of services provided at a facility, a patient evaluates, via an information station located at/near the facility, the recently provided services. The patient also responds to questions pertaining to the provided services. This information is collected via the information station contemporaneously with the visit to the facility. In an example embodiment, the patient is provided, via the information station, auxiliary information such as information about prescribed medications, self care, health insurance regulations, billing, or the like, for example.

BRIEF DESCRIPTION OF THE DRAWINGS

The foregoing and other objects, aspects and advantages of patient-interactive healthcare management will be better understood from the following detailed description with reference to the drawings.

FIG. 5 is an illustration of a patient's perceptions of interactions with a healthcare practitioner.

FIG. 12 is an illustration of an example survey comprising patient healthcare guidance information.

FIG. 13 is an illustration of an example survey comprising a reference to an activity list.

FIG. 14 depicts an example activity list.

FIG. 15 depicts another example activity list.

DETAILED DESCRIPTION OF ILLUSTRATIVE EMBODIMENTS

Figure 1:
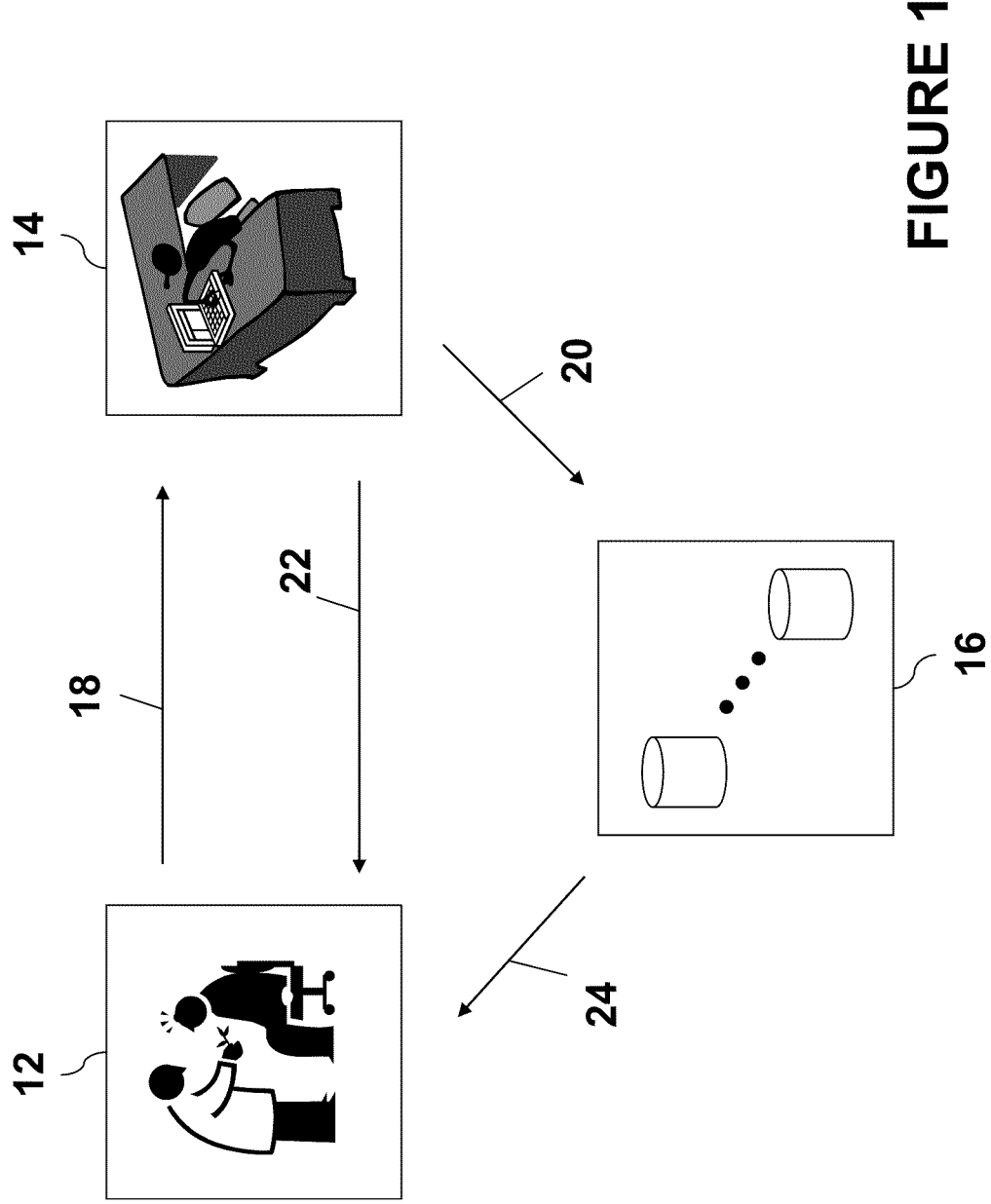
FIG. 1 is a depiction of an example scenario involving patient interactive healthcare management.

Healthcare is managed via patient interaction at the time the patient is visiting a health care facility to receive healthcare services and/or goods. As used herein, the phrase "healthcare services" refers to healthcare services and/or healthcare goods. Patient-interactive healthcare management as described herein has numerous application, including, for example, home health, skilled nursing, assisted living, hospice, teaching facilities, dental healthcare, holistic healthcare, mental healthcare, occupational healthcare, physical rehabilitation, and healthcare related encounters between patient/consumer and a practitioner/provider.

In an example embodiment, this contemporaneous interaction includes assessing the quality of provided health care services and verifying the accuracy of an invoice, prebill, bill, charge ticket, or the like, listing the services provided. Additionally, information can be provided to the patient to educate the patient about healthcare and about actions the patient can take to improve her/his health. The results of the patient's interaction are provided to a database for storage, to a third party responsible for paying at least a portion of the rendered services/goods, an agency for collecting health care information, the healthcare facility that provided the services/goods, or a combination thereof. Providing results and comparisons of the patient's interaction in this manner (e.g., feedback) can result in improvements in patient and healthcare provider behavior.

Patient-interactive healthcare management as described herein can help Federal and State governments, private practices, employers, and/or patients improve the quality and cost of healthcare. In an example embodiment, patient-interactive healthcare management is a web based, multimedia resource, programmed to gather useful patient and provider data using the patient's energy via surveying the patient at the end of the doctor visit. Various embodiments of patient-interactive healthcare management also can be programmed to provide periodic consumer reports to the patient. Example consumer reports include local reports, regional reports, national reports, physician office customer satisfaction reports, and statistics such as the number of procedures performed by a physician per period of time (year, month, etc.), or a combination thereof. In other example embodiments, patient-interactive healthcare management provides patient education information, and is usable to propagate public awareness about ways to more wisely manage healthcare resources. In an example embodiment, patient-interactive healthcare management is a consumer driven, point-of-service tool which can be placed in a healthcare facility, to empower government-pay beneficiaries to exercise normal buying behaviors. When a patient sees a practitioner (e.g., physician, nurse, physician's assistant, psychologist, psychiatrist, physical therapist, or the like), patient-interactive healthcare management allows the patient/consumer to express the level of satisfaction with the quality of care received, and to verify that specific services were rendered during the visit.

FIG. 1 is a depiction of an example scenario involving patient interactive healthcare management. At scene 12 of the example scenario, the patient is provided healthcare services (e.g., physical, electrocardiogram, stress test) and goods (e.g., sample medication, a prescription for medication, a prescription for follow up service such as blood work) by the physician. After receiving the services/goods, the patient goes to (step 18) the information station depicted at scene 14. At the information station, as described in more detail below, the patient answers questions about the quality of the provided healthcare services. Also at the information station, the patient verifies the accuracy of an invoice, prebill, bill, charge ticket, or the like, of the provided services/goods. Information gathered from the patient via the information station is provided (step 20) to an entity 16 such as a database, a third party, a government agency, or the like. The results collected from the patient are indicative of a verified record of services provided to the patient and provide for the collection of contemporaneous feedback on the quality of the service received and patient compliance with prescribed conduct. Thus allowing for feedback regarding the level of congruence between doctor/nurse practitioner instruction and/or practice of evidence based medicine and patient's understanding and inclusion of the same. The information gathered from the patient also can be provided (step 22) to the facility/physician that provided the services/goods. Upon analysis of the received information, the entity 16 can provide (step 24) payment and/or feedback to the facility that provided the services/goods.

Figure 2:
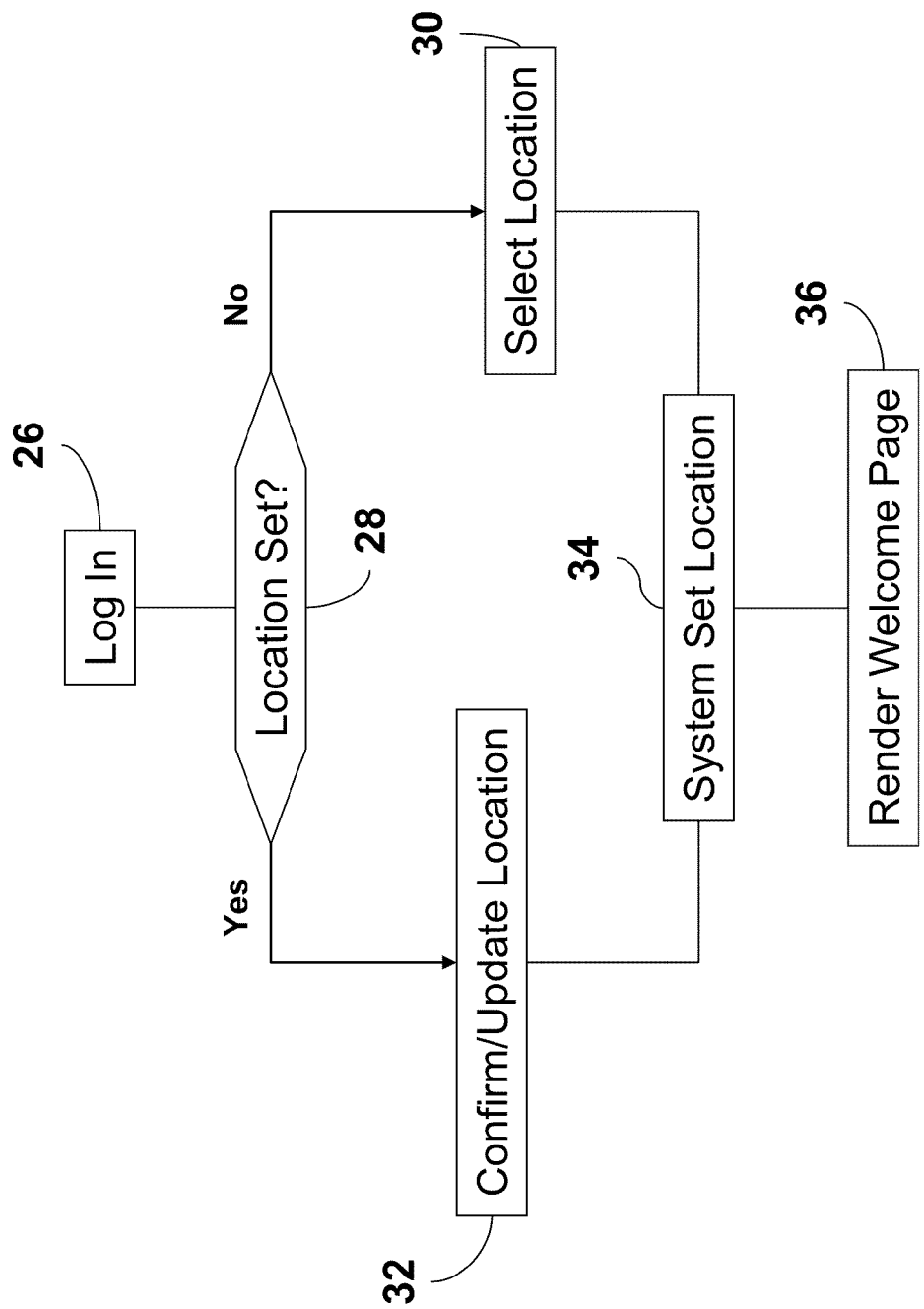
FIG. 2 is a flow diagram of an example process for setting the location of a healthcare facility.

FIG. 2 is a flow diagram of an example process for setting the location of a healthcare facility within the system for implementing patient-interactive healthcare management. After receiving healthcare services, the patient logs in at step 26. In an example embodiment, the patient logs in at the information station. At step 28, it is determined if the location at which the patient received the healthcare services is set in the system. If the location is set within the system (step 28), the location is confirmed at step 32. T and he location also can be updated as to 32. If the location is not set (step 28) in the system, location is selected by the patient at step 30. At step 34, the location set into the system. At step 36, a welcome page, or the like, is rendered. The welcome page can comprise any appropriate page from which the patient can start completing the survey, selecting providers, or the like.

Figure 3:
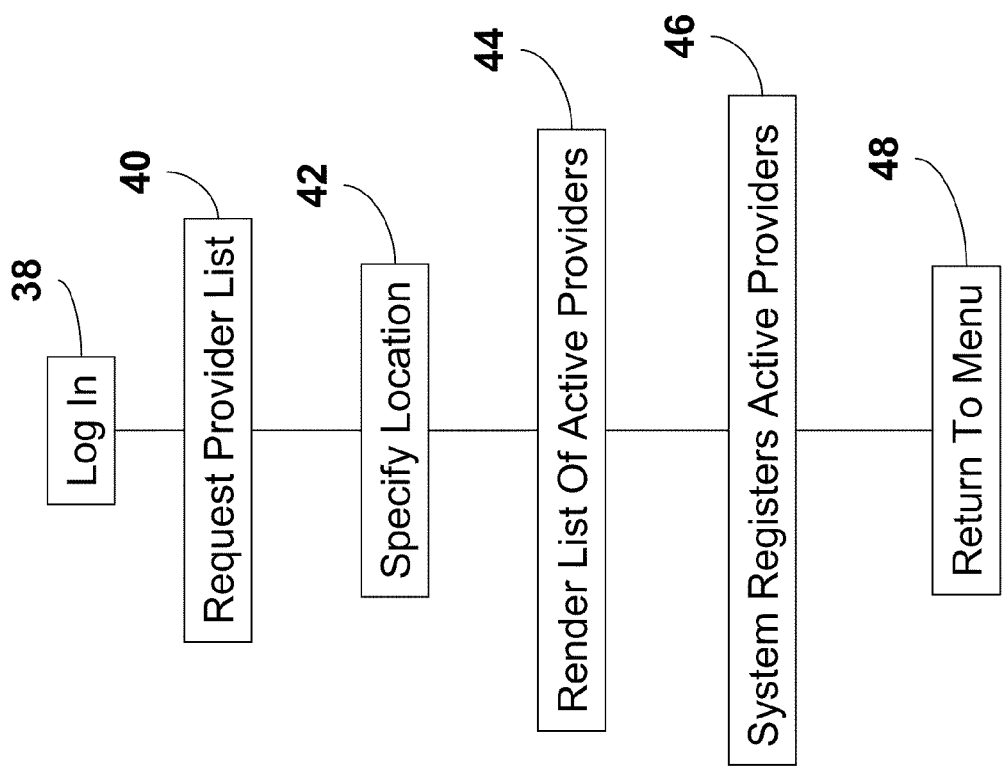
FIG. 3 s a flow diagram of an example process for establishing a list of healthcare providers.

FIG. 3 is a flow diagram of an example process for establishing a list of healthcare providers. The patient logs into the system instead 38. In an example embodiment, the patient logs in at the information station. The patient requests a provider list at step 40. At step 42, the patient provides the location of the healthcare facility at which the healthcare services were rendered. Step 44, a list of active providers associated with the specified location is rendered via the system. At step 46, the active providers are registered with the system. The patient is returned to the main menu at step 48. At the main menu, the patient can start completing the survey.

Figure 4:
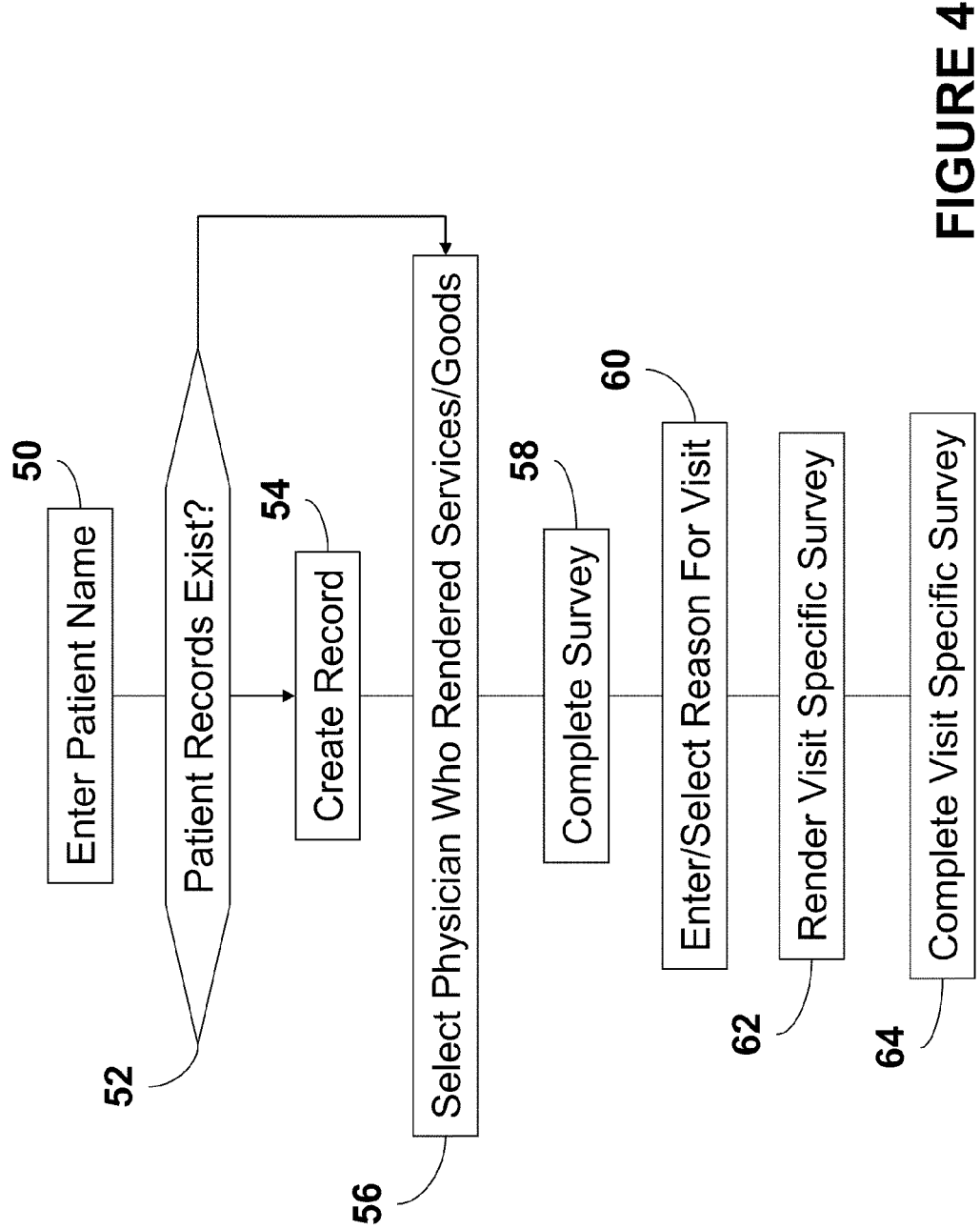
FIG. 4 is a flow diagram of an example process for completing a survey.

FIG. 4 is a flow diagram of an example process for completing a survey. The patient enters her/his name at step 50. At step 52, it is determined if the patient's records are in the system. If the patient's records are in the system (step 52), the process proceeds to step 56. If the patient records are not in the system (step 52), the process proceeds to step 54. At step 54, a record is created for the patient. At step 56, the patient selects, from a provided list of physicians, the physician who rendered the services/goods. As described in more detail below, the patient completes the survey asked at 58.

In an example embodiment, the patient can complete a survey pertaining to health care issues associated with the specific visit. For example, if the healthcare visit pertains to diabetes, a survey pertaining to diabetes can be completed. In accordance with this embodiment, at step 60 the patient enters, or selects from a provided list, the reason for the visit. At step 62, the survey is provided by the system. At step 64, the patient completes the visit specific survey.

Figure 5:
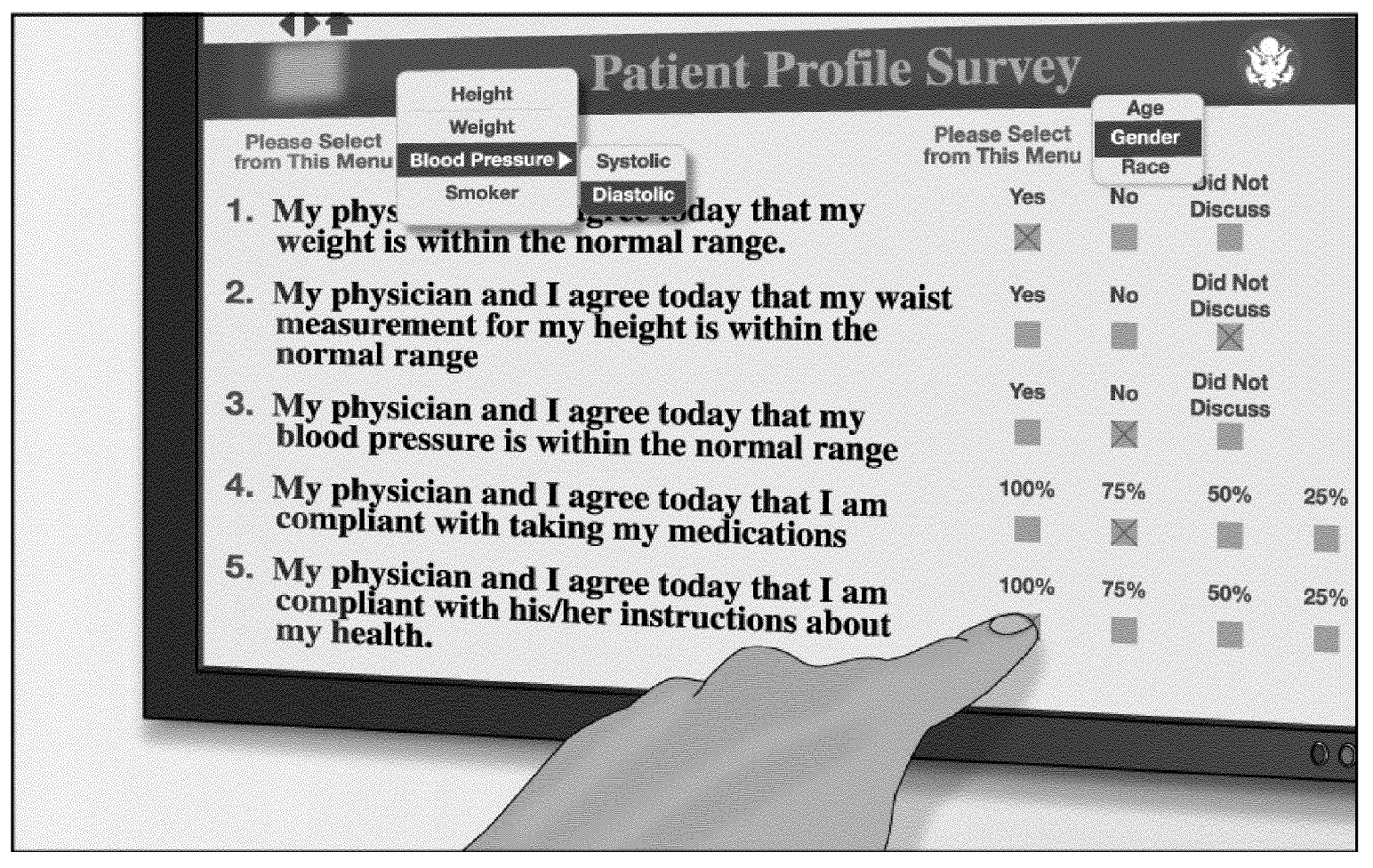

Via the information station, in an example embodiment, the patient interacts with a user prompted interface. As depicted in FIG. 5, the information station collects information from patients via a touch screen. In an example embodiment, a survey is conducted, using non-specialized language, about the patient's experience during the visit. The patient's perceptions pertaining to the quality of the current physician visit is gathered. Patient's perceptions of the communication of health topics in the delivery of evidence based health care during the physician visit also are collected.

In an example embodiment, administered healthcare services are verified by the patient immediately after treatment. This can reduce incidences of health care fraud because health insurance companies will be presented with accurate information as to the medical services that were actually rendered. Because the consumer/patient provides an evaluation of the office visit contemporaneously with the visit, using the consumer's energy/knowledge is likely to be a reliable source to pinpoint and reduce billing mistakes and attempts at fraud. The patient/consumer is also the best qualified to comment on the treatment received during the office visit. Information gathered from the patient, via the information collection station, provides the ability to simplify fraud prevention activities, gather physician office best practice data, and to gain patient education at the time of their visit.

For example, in accordance with the scenario depicted in FIG. 1, after the patient completes her physician's visit, a staff member says, "Can I ask you to come to the patient waiting room so that you can complete a brief survey?" Moments later, the patient is seated at a computer console with a touch screen, where she taps in answers to a set of questions pertaining to her satisfaction with her care during the visit and several other questions about her choices in diet, exercise, and personal care. The patient is then asked to confirm that the list of procedures identified in the invoice, prebill, bill, charge ticket, or the like, to her insurance company was actually completed during the visit. The staff member then says to the patient, "Thanks for completing the survey today. Your answers will be sent electronically to your insurance company, the quality control office for this medical group, and/or to the Centers for Medicare and Medicaid Services for compilation into a national database. Confidentiality will be appropriately maintained. And here is a copy for you, with a few notes from the doctor about some things you can do to manage your current health condition." The copy also, or in the alternative, can be made available via electronic means (e.g., Internet).

Figure 6:
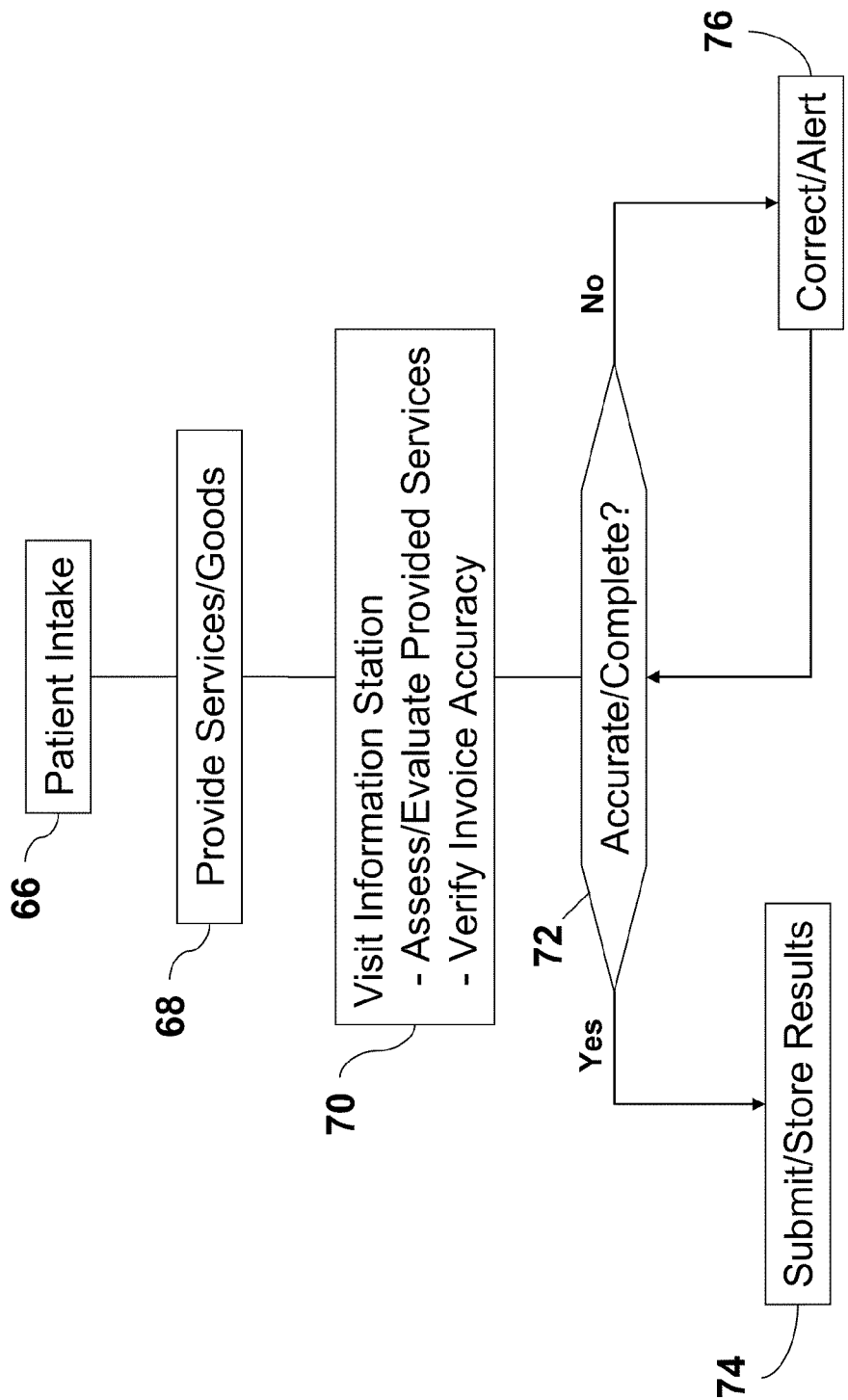
FIG. 6 is a flow diagram of an example process for providing patient-interactive healthcare management.

FIG. 6 is a flow diagram of an example process for providing patient-interactive healthcare management. At step 66, a patient is taken into a healthcare facility. Patient intake can include, for example, the patient signing in at the healthcare facility. At this point, the healthcare facility is aware of the patient's presence and can retrieve any files, records, or the like related to the patient. Healthcare services are provided at step 68. For example, the patient can see the physician and receive treatment, such as a physical examination, or the like.

At step 70, the patient visits the information station. At the information station, the patient assesses the quality of the provided services and verifies the accuracy of an invoice, prebill, bill, charge ticket, or the like, of the provided services/goods. In an example embodiment, the patient receives, via the information station, an invoice, prebill, bill, charge ticket, or the like, comprising an itemized list of healthcare services provided. The patient can receive the invoice, prebill, bill, charge ticket, or the like, by providing identifying information via the information station. Example identifying information can include the patient's name and/or an account number associated with the patient. Identifying information can be entered via a keyboard, mouse, or the like, via the information station, and/or identifying information can be provided via a storage device such as a patient identification card, common access card, or the like.

In an example embodiment, the invoice, prebill, bill, charge ticket, or the like, is provided to the patient before the patient visits the information station. For example, the treating physician or a staff member can provide the invoice, prebill, bill, charge ticket, or the like, to the patient while walking the patient to the information station.

If the invoice, prebill, bill, charge ticket, or the like, was prepared properly, the invoice should accurately reflect the administered healthcare services/goods. The invoice, prebill, bill, charge ticket, or the like, can include identification of each service rendered, such as a textual description (e.g., physical examination) and/or codes such as CPT (Current Procedural Terminology) codes. For example, a standard physical examination may have a code of #123. The invoice also can indicate the fee associated with each itemized service and/or good.

At the information station, if the patient was provided the invoice, prebill, bill, charge ticket, or the like, prior to visiting the information station, the patient provides the information station with the patient's copy of the invoice, prebill, bill, charge ticket, or the like. For example, the patient can place the invoice on a scanning bed for electronic scanning. The invoice, prebill, bill, charge ticket, or the like, can be scanned and the information station can determine the itemized services written on the invoice. The contents of the invoice, prebill, bill, charge ticket, or the like, can also be loaded into the information station via computer keying (either by the patient or the doctor/staff, or it can be digitized (scanned) by the staff and retrieved at the information station.

In an example configuration, the information station comprises an output device, such as a display, a speaker, or a combination thereof for rendering a list of services/goods matching the itemized services/goods identified on the invoice, prebill, bill, charge ticket, or the like,. The patient verifies the accuracy of the invoice, prebill, bill, charge ticket, or the like, by reviewed the rendered list and providing an indication as to the accuracy thereof For example, the patient, via an input device (e.g., a keyboard, mouse, buttons, touch screen) can confirm that the rendered list of services accurately reflects the actually administered services. This can be accomplished, for example, by the patient pressing "yes" button to confirm or a "no" button, otherwise. The information station having a visual output device and an audio output device allows patients having visual or hearing impairments to utilize the information station. Thus, a patient with a visual disability can listen to the rendered list of services/goods and verify the accuracy thereof accordingly.

If the patient indicates (step 72) that the invoice, prebill, bill, charge ticket, or the like, is accurate, a list of verified services/goods is submitted to the appropriate entity at step 74. The invoice, prebill, bill, charge ticket, or the like, can also be submitted along with the list. If the patient indicates (step 72) that the invoice, prebill, bill, charge ticket, or the like, is inaccurate, the inaccuracy(s) can be corrected (or reconciled later) at step 76. The process proceeds to step 32 therefrom. For example, if the patient confirms (step 72) that the rendered list of services is accurate, the verified list of services/goods (and optional invoice, prebill, bill, charge ticket, or the like,) can be provided to the third party, at step 74, for payment of the services. If the patient indicates that the rendered list of services is inaccurate, the healthcare facility (e.g., an employee of the office including the physician) can be alerted that there is a discrepancy with the invoice. The employee can review the invoice, prebill, bill, charge ticket, or the like, correct any discrepancy(s), and allow the patient to confirm the accuracy (at step 32) of the corrected invoice, prebill, bill, charge ticket, or the like.

In an example embodiment, upon completion of authentication and verification of the providers charge for services, the patient can provide a signature (e.g., electronically). Over time with repetitive use the patient will enhance her/his healthcare literacy and become more familiar with the medical terminology used to describe the care she/he receives and the cost associated with the service. Beginning with the collection of charge-to-patient services, by patient, by doctor, these metrics can populate a database for customers and consumers to access. Because the method of data gathering is simple, affordable and natural, using it makes the defensibility against billing mistakes, fraud, and abuse more easily achievable.

In an example embodiment, patient-interactive healthcare management can be used to supplement existing standard billing practices. For example, currently, a doctor's office submits a copy of an invoice to a health insurance company for reimbursement. This can still be done and the information station can also be used to verify, to the health insurance company, that the invoice is accurate. The health insurance company can compare the invoice received from the healthcare facility with the list that is received (at step 34), and if there is a match, the invoice can be processed normally.

Patient-interactive healthcare management as described herein provides a patient (e.g., a government-pay patient such as a Medicare patient or a Medicaid patient) the ability to exercise true normal buying behavior. Customer verification allows the patient to approve immediate payment in full to a physician for the services just received and verified. Typically, getting paid immediately is a benefit that providers will welcome. Unlike most vendor transactions, healthcare providers do not get paid in full at the time their services are rendered. Paying them "immediately" is a motivating benefit. The patient-interactive healthcare management system provides a mechanism for providing co-pay versus charges and/or co-pay versus costs.

Figure 7:
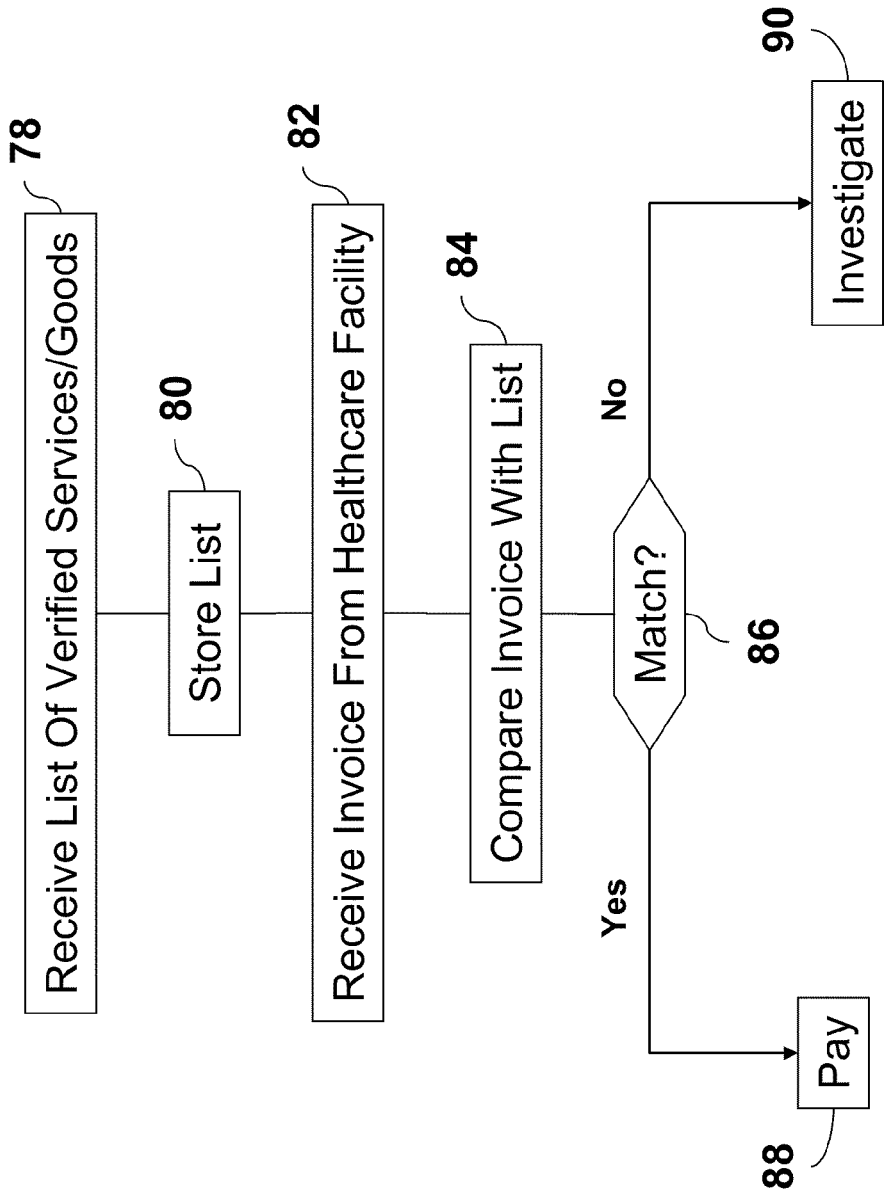
FIG. 7 is a flow diagram of an example process for verifying healthcare services and/or goods.

FIG. 7 is a flow diagram of an example process for verifying healthcare services. At step 78, the payer (e.g., a health insurance company, a government agency, a third party) receives the verified list of healthcare services (e.g., the verified list provided at step 74). At step 80, the payer stores the verified list in a database or the like. At step 82, the payer receives the invoice from the healthcare facility. The invoice can be provided to the payer concurrent with the verified list and/or separately. The invoice can be physically mailed and/or electronically transmitted to the payer for payment. The payer compares, at step 84, the received invoice with the verified list. If the verified list matches (step 86) the invoice, the payer pays the appropriate portion of the invoice at step 88. If the verified list does not match (step 86) the invoice, the payer does not pay the invoice, and can optionally investigate, at step 90, why the verified list does not match the invoice. Because the verified list was contemporaneously verified (e.g., step 70) by the patient during the visit to the healthcare facility, the payer is provided a high confidence level that the invoice is accurate if it matches the verified list.

Figure 8:
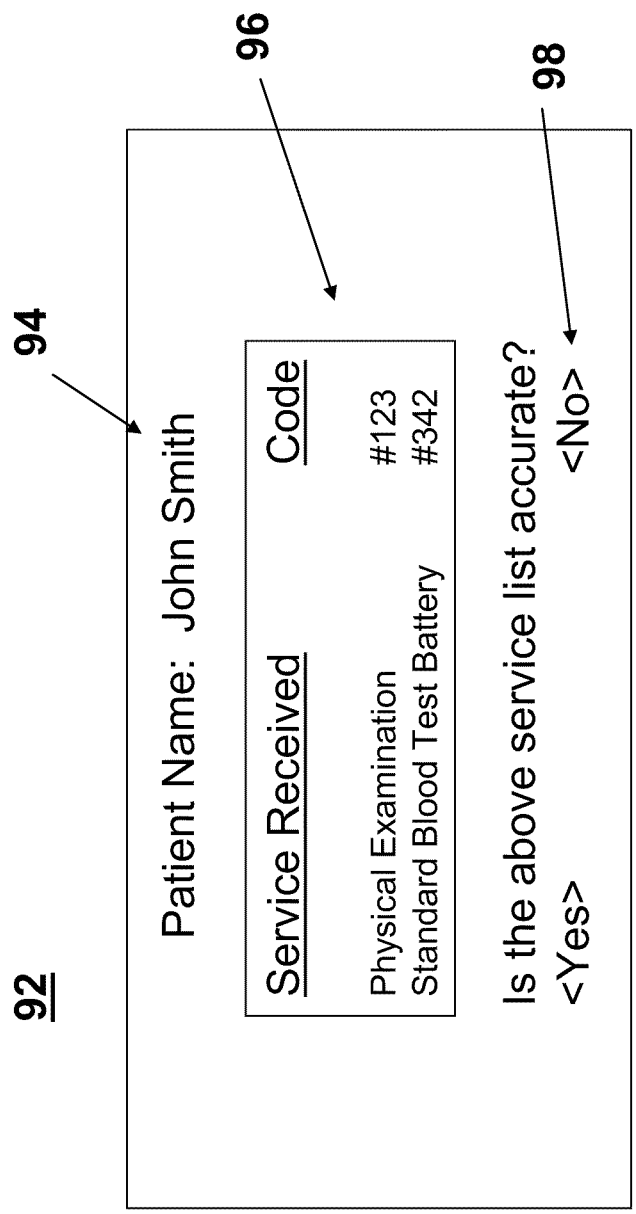
FIG. 8 is a depiction of an example confirmation screen for verifying healthcare services/goods.

FIG. 8 is a depiction of an example confirmation screen 92 for verifying healthcare services/goods. Prior to viewing the screen 92, the patient can be verified. Verification can be accomplished via any appropriate means for example, via interface with the payor, via a common access card, via a patient identification card, and/or via any applicable ID authentication system. The confirmation screen 92 can be visually displayed, for example on a display device of the information station, the confirmation screen 92 can be provided as a hardcopy (printed version of confirmation screen), the confirmation screen 52 can be provided via audio, or a combination thereof The confirmation screen 92 comprises a portion 94 for providing a name of the patient, a portion 96 for providing a list of healthcare services/goods, and a verification portion 98 for allowing the patient to verify the list of healthcare services/goods. Portion 94 can provide the patients name and any other related information, such as the patient's health care provider, for example. The portion 96 can provide a list of the services rendered, and any associated codes. The verification portion 98 provides the patient an opportunity to confirm that the list (portion 96) is accurate by allowing the patient to touch a "yes" button or a "no" button.

Figure 9:
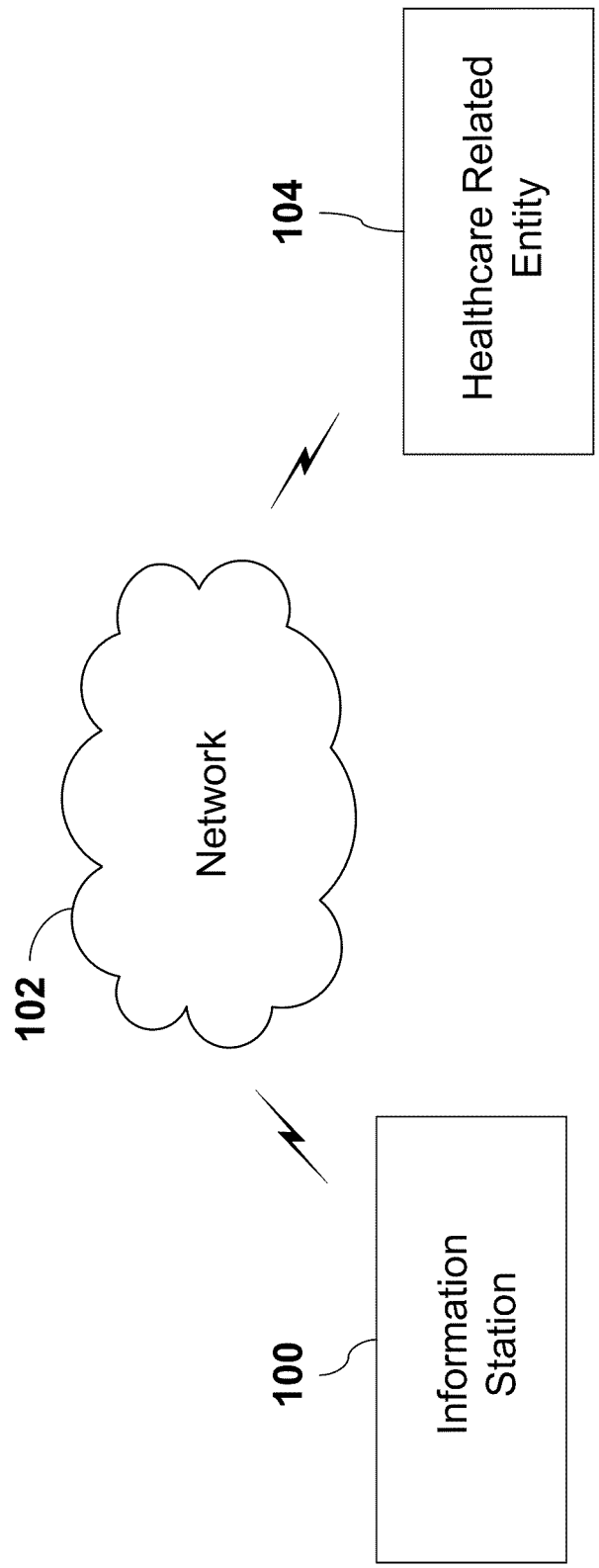
FIG. 9 is a diagram of an example system for implementing patient-interactive healthcare management.

FIG. 9 is a diagram of an example system for implementing patient-interactive healthcare management comprising the information station 100 and a healthcare entity 104 (e.g., a health insurance company, a government agency, a healthcare data collection entity). In an example configuration, an information station 100 is located in a healthcare facility, such as a physician's office, a clinic, a hospital, or the like. The information station communicates with the healthcare entity, or entities, 104 via a network 102. The network 62 can comprise any appropriate network such as a wired network, a wireless network, an optical network, or a combination thereof. For example, the network 102 can comprise an Internet, an intranet, a LAN (local area network), or a combination thereof. In an example embodiment, the healthcare related entity 104 is the entity to which the list of verified services is sent.

In an example configuration, information provided from and/or received by the information station 100 can comprise secure information. For example, information can be encrypted, obfuscated, or a combination thereof. Any appropriate techniques can be used to secure information, such as symmetric key encryption, public key encryption, or a combination thereof.

In some cases, a patient may have multiple insurance companies. For example, the patient may be a member of the Veteran's Association which may contribute to a portion of a patient's medical bills. The patient may also have a primary health insurance company as well. The embodiments described herein in which payment can be made to a respective health insurance company can also be applied to multiple health insurance companies, credit card companies, reconciliation companies, or the like. In this way, all health insurance companies (either public or private) can be reimbursed electronically and automatically. Thus, as depicted in FIG. 9, the healthcare related entity 104 can comprise a single entity or multiple entities.

Figure 10:
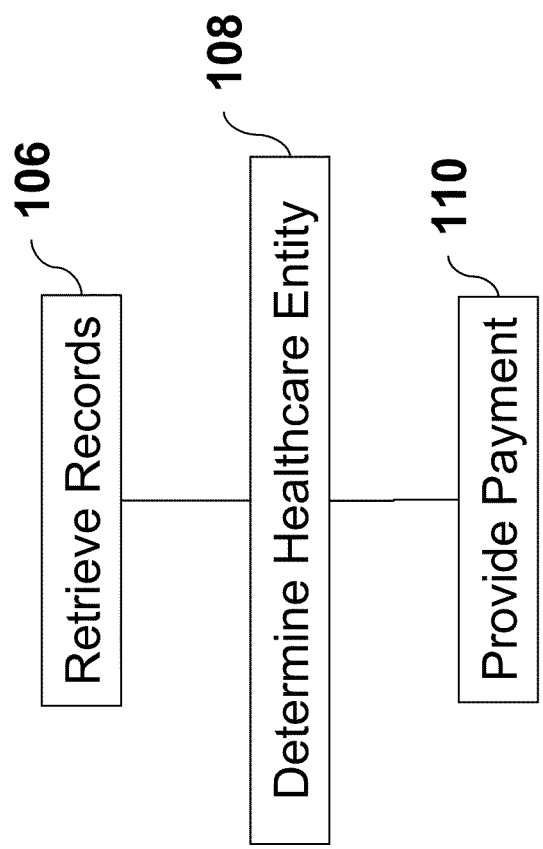
FIG. 10 is a flow diagram illustrating an example process for identifying and disbursing funds to multiple entities.

FIG. 10 is a flow diagram illustrating an example process for identifying and disbursing funds to multiple entities. At step 106, patient records are retrieved. Patient records can be located and retrieved via any appropriate means, such as electronically retrieving a record about the patient from any relevant database or storage, for example. Storage can comprise any appropriate storage, such as a database (e.g., physician's database, a remote database from the patient's primary health insurance provider, or any database which may have access to the patient's health insurance provider(s)), a storage facility, local memory of a processor, or a combination thereof. Storage can include a non-electronic record of the patient's health insurance companies garnered from a physical patient questionnaire that the patient may have completed. Retrieval of records also can include retrieving rules associated with provider's responsibilities for paying invoices.

At step 108, it is determined which healthcare entities (e.g., health insurance company) are associated with the patient. This can be accomplished by retrieving information in the located/retrieved records (step 106) about the health insurance provider(s) that the patient is associated with. The rules that apply to the health insurance provider(s) can also be stored therein so that the system knows how much each health insurance company should pay. Payment(s) is provided at step 110. The payment amounts can be calculated based on the rules associated with each provider. Thus, if the patient has multiple health insurance providers, each provider can be automatically paid the appropriate amount. For example, a patient's primary health insurance provider may cover 80% of the invoice, and a secondary provider may cover 15% of unreimbursed expenses. Thus, if this patient's medical bill is $100, $80 would be covered by the primary health insurance provider and $15 would be covered by the secondary provider. The remaining $5 may have to be covered by the patient himself.

In an example embodiment, results of the patient's evaluation of the rendered services/goods are provided (fed back) to healthcare providers, healthcare benefactors, and/or healthcare recipients in order to impact healthcare behavior. Additionally, reinforcement of suggested behavior is provided. Patient and healthcare provider data is gathered using consumer (rather than provider) energy, by surveying patients at the end of the physician office visit. The patient-interactive healthcare management as described herein gathers information regarding patient perceptions of their visit and health goals, and provides immediate feedback and patient education information to propagate public awareness about ways to more wisely manage healthcare resources. Patient-interactive healthcare management delivers comparative peer group data designed to improve consumer disease prevention education and patient self-management skills. Patient-interactive healthcare management also collates consumer satisfaction reports and physician procedure data that can be used by benefactors. The real-time collection of patient-centric data extends the capability of benefactors to evaluate and react to provider performance, thereby enhancing the infrastructure needed to administer benefactor programs. Patient-interactive healthcare management provides to physicians and healthcare providers means to meet electronic compliance requirements, the capability to acquire an immediate payment for services, and is a patient point-of-service tool to obtain and evaluate customer satisfaction opinions.

Figure 11:
FIG. 11 is an illustration of an example verification survey.

In an example embodiment of patient-interactive healthcare management, after healthcare services are rendered to the patient, the patient is provided, via the information station, a survey about the patient's experience. For example, the patient can be asked questions relating to the patient's evaluation of the visit with the physician, such as waiting time, confidence in the physician, quality of the treatment, or the like. In an example embodiment the survey is utilized to verify services provided for payment and quality of services for consumer information. If the patient verifies and is satisfied with the services provided, the patient authorizes immediate payment, as depicted in FIG. 11. The surveys and payment information can be collected on a database or any appropriate storage means. Responses to the survey can be tabulated and provided to the physician's office (healthcare facility).

The survey offers government-pay patients (e.g., Medicare, Medicaid) the opportunity to express concerns and satisfactions with the care received from their attending healthcare professional (e.g., physician). The information provided by the patient can be aggregated into a database, or the like, that can be used to report a customer satisfaction score by provider, for customers and consumers accessible from a website, network, or the like. As the patient survey evolves it can yield comparative disease state management data intended to educate individuals about ways to reduce individual risk factors and achieve self-efficacy. This information can be converted into disease state management profiles that direct specific attention to various levels of analysis for the individual, the public, and the government-payer.

FIG. 12 is an illustration of another example survey form comprising information pertaining to patient self care. As depicted in FIG. 12, the patient is asked questions pertaining to the rendered healthcare services and pertaining to the patient's intentions to comply with healthcare instructions. The patient also is asked if she/he has any questions. If the patient has questions, the questions can be answered at the time the patient is completing the survey. Additionally, as depicted in FIG. 12, the patient is provided information pertaining to healthcare issues relating to the rendered healthcare services/goods. In the example depicted in FIG. 12, the patient received healthcare services/goods related to diabetes.

Additionally, the patient can be provided an activity list comprising a list of activities to be conducted after the patient leaves the physician's office. FIG. 14 depicts an example activity list for a patient having diabetes. FIG. 15 depicts an example activity list for general therapeutic healthcare activities. For example, the activity list can be referenced in the survey form as depicted in FIG. 13.

In an example embodiment of patient-interactive healthcare management, patient and physician event data are gathered and utilized to develop individual and/or aggregate healthcare trends and/or statistics. The trend information can be utilized to gain insights about patient experiences. This information is utilizable to differentiate patterns among patients and physicians. The information offers perspectives on aspects of customer satisfaction, health-related self-care, and the individual and collective financial transparency needed to amplify the cost associated with patient and physician events. This information is updatable to allow observation of new insights into changing behaviors.

Patient-interactive healthcare management as described herein enhances the awareness of patients, and consumers, of healthcare issues. By enabling the patient to communicate with the physician and the insurer about the quality of the patient experience, the patient becomes more aware of national data about satisfaction, and about information about the qualifications of physicians. As an informed consumer, it is reasonable to expect patients to adapt socially responsible behaviors to reduce costs and improve quality by engaging in the choice of provider, and in the choice of interventions proposed by the provider. Via utilization of patient-interactive healthcare management, providers, payers, and consumers will be able to more wisely manage healthcare resources.

In an example embodiment, the patient can submit a personal email address, via the information station. Update can, to which updates will be sent about physician ratings, information about common disease states for the patient's age and gender, regional alerts for communicable diseases, and on-call information about treatment options for specific diagnoses.

Patient participation in patient-interactive healthcare management can create a heuristic for patient satisfaction information; as each patient enters a survey, the total national database is automatically updated, so that at any time authorized researchers can get an up-to-date insight into recent trends in patient perceptions, and benchmark best practices. The bond which this system creates among the patient, the physician and the payer benefits all participants; the physician learns what her/his patients feel about the office experience, the payer obtains data to identify trends and to verify the validity of claims, and the patient is permitted to expand her/his capacity as a responsible purchaser of health services. Customers of patient-interactive healthcare management can include the federal, state, and local governments, which can license its use, and the health-care providers who participate in public-pay systems. A web site that can display data collected in patient surveys can be a consumer-driven website which uses the consumer's energy to create useful patient and provider trending data. This encounter trending will help the consumer to analyze provider pricing and service quality data and to adopt cost-effective health behaviors. This system is independent from the provider or the provider's staff This system provides a uniform data set and the ability to easily update, modify or change the data set by the control group licensing its application. Having the means to incorporate and modify a uniform data set will allow national, state, and local managers the ability to cross walk specific cause and effect realities that are or are not working at the provider/patient level.

In an example embodiment, therapeutic, educational intervention is conducted at an appropriate time contemporaneously with the healthcare visit in order to promote positive change in patient and/or physician behavior. In an example embodiment, as the rendering of healthcare services is upon completion, the physician segues into a brief, effective intervention with the patient. During the intervention, the patient can be provided educational material, can be provided a questionnaire, can engage in a conversation with the physician, or a combination thereof.

In an example therapeutic intervention, the physician can ask the patient if the patient is satisfied with the treatment received. The physician can ask the patient if the patient will adhere to instructions provided. The physician can ask the patient if the patient has any questions. Additionally, the physician can reinforce preventative medicine and/or chronic disease points of self-care with the patient by providing, for example, the activity list depicted in FIG. 14 and FIG. 15. Further, the physician can encourage the patient to participate in the evaluation process. Upon completion of the intervention, the patient can progress to the information station to evaluate the rendered services.

Figure 16:
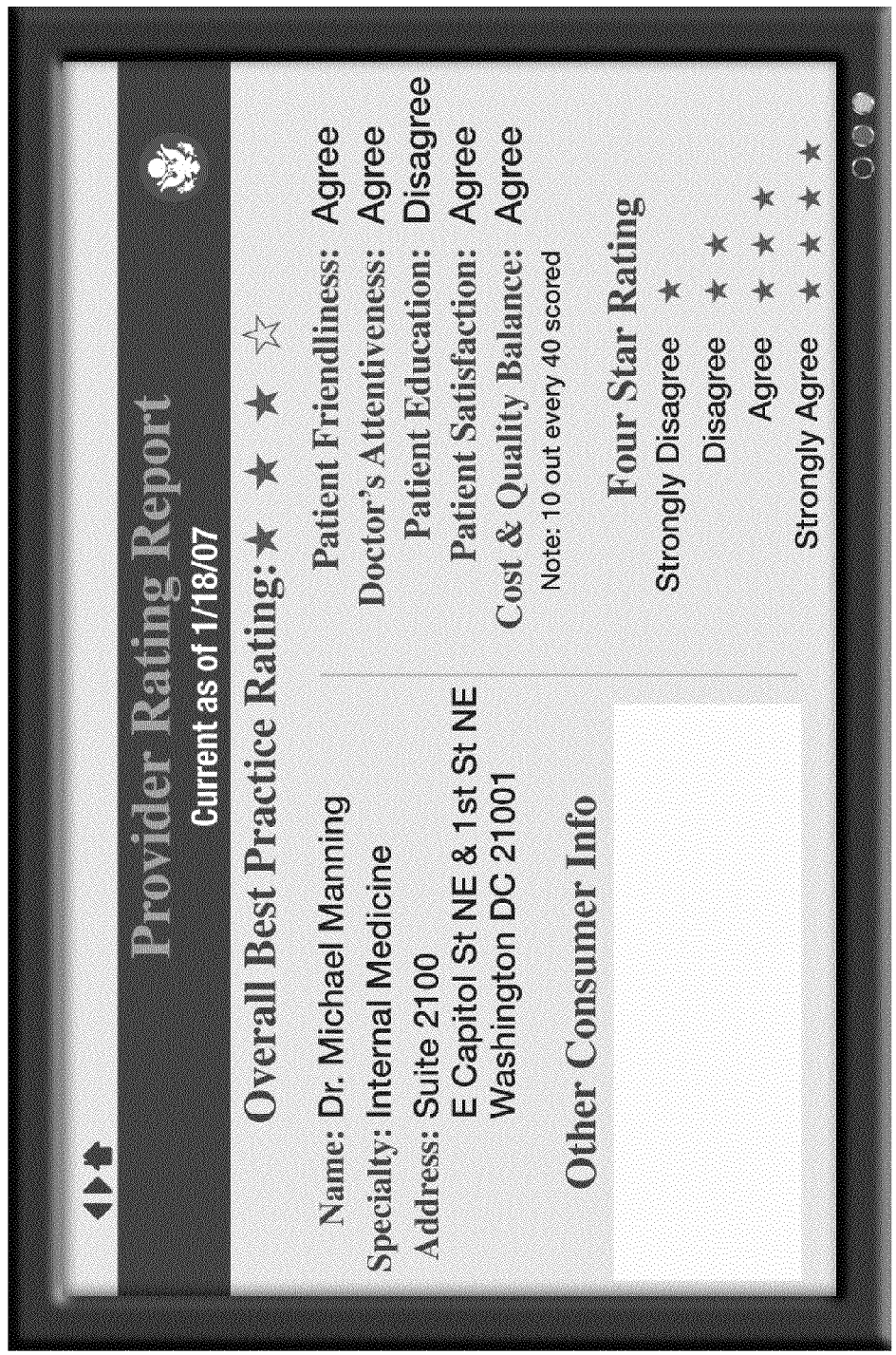
FIG. 16 is a depiction of an example provider rating report.

FIG. 16 is a depiction of an example provider rating report. In an example embodiment, providers are rated and the ratings are made available. The provider rating report depicted in FIG. 16 can be made available via the Internet, via email, via a paper report, or like. Consumers can utilize the provider rating reports to assess practitioners before or after receiving services from the practitioner. A provider rating report can be generated from the evaluations and/or ratings of multiple patients. Information included in a provider rating report can include, for example, an assessment of the friendliness of the practitioner, the practitioner's attentiveness to patients, an assessment of the education received from the practitioner, patients' overall satisfaction with a practitioner, and an indication of patients' perception of cost and quality of rendered healthcare services/goods.

Figure 17:
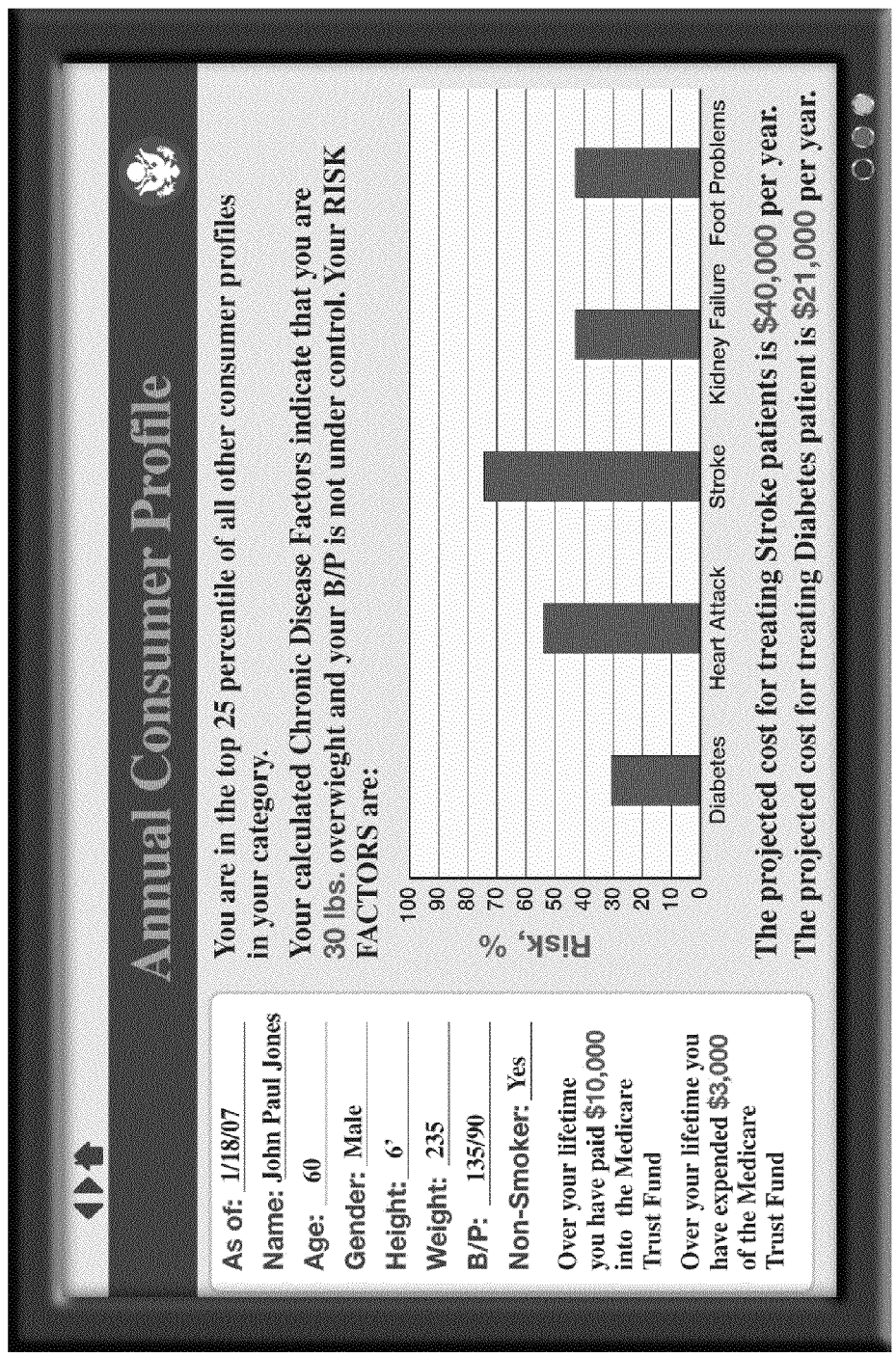
FIG. 17 is a depiction of an example consumer profile.

FIG. 17 is a depiction of an example consumer profile. The consumer profile is indicative of a patient specific healthcare report. In an example embodiment, the patient-interactive healthcare management system stores and maintains healthcare information pertaining to each consumer's experiences. A consumer can access a profile containing such healthcare information. The consumer profile depicted in FIG. 17 is an annual consumer profile. However the profile can be indicative of any appropriate amount of time. The consumer profile can provide information such as the consumer's name, age, sex, and physical characteristics. The consumer profile can provide statistics pertaining to specific healthcare issues. For example, the consumer profile can provide information pertaining to chronic disease factors such as indication as to whether the consumer is within acceptable weight boundaries and/or whether the patient's blood pressure is under control. The consumer profile can provide information indicative of patience risk factors pertaining to various ailments such as diabetes, heart attack, stroke, kidney failure, and foot problems, for example. Additionally, the consumer profile can run information pertaining to cost for treating specific ailments.

In an example embodiment, the patient interactive healthcare management system can be utilized as an information repository for tracking purposes. For example, the patient-interactive healthcare management system can be utilized to track durable medical equipment or the like. For example, a patient may receive a durable medical product such as a wheelchair to during her visit to the healthcare practitioner. At the information station, or the like, a barcode affixed to the wheelchair can be scanned into the patient interactive healthcare management system. This system will associate the wheelchair with the patient can maintain this information for tracking purposes. When the patient no longer needs the wheelchair, the patient can return the wheelchair to the practitioner, or to any appropriate location, and the location of the return wheelchair will be updated in the patient-interactive healthcare management system. The patient interactive healthcare management system also can be utilized to track prescriptions. Does, the patient interactive healthcare management system can function as a repository for tracking and maintaining a patient's medication use.

Figure 18:
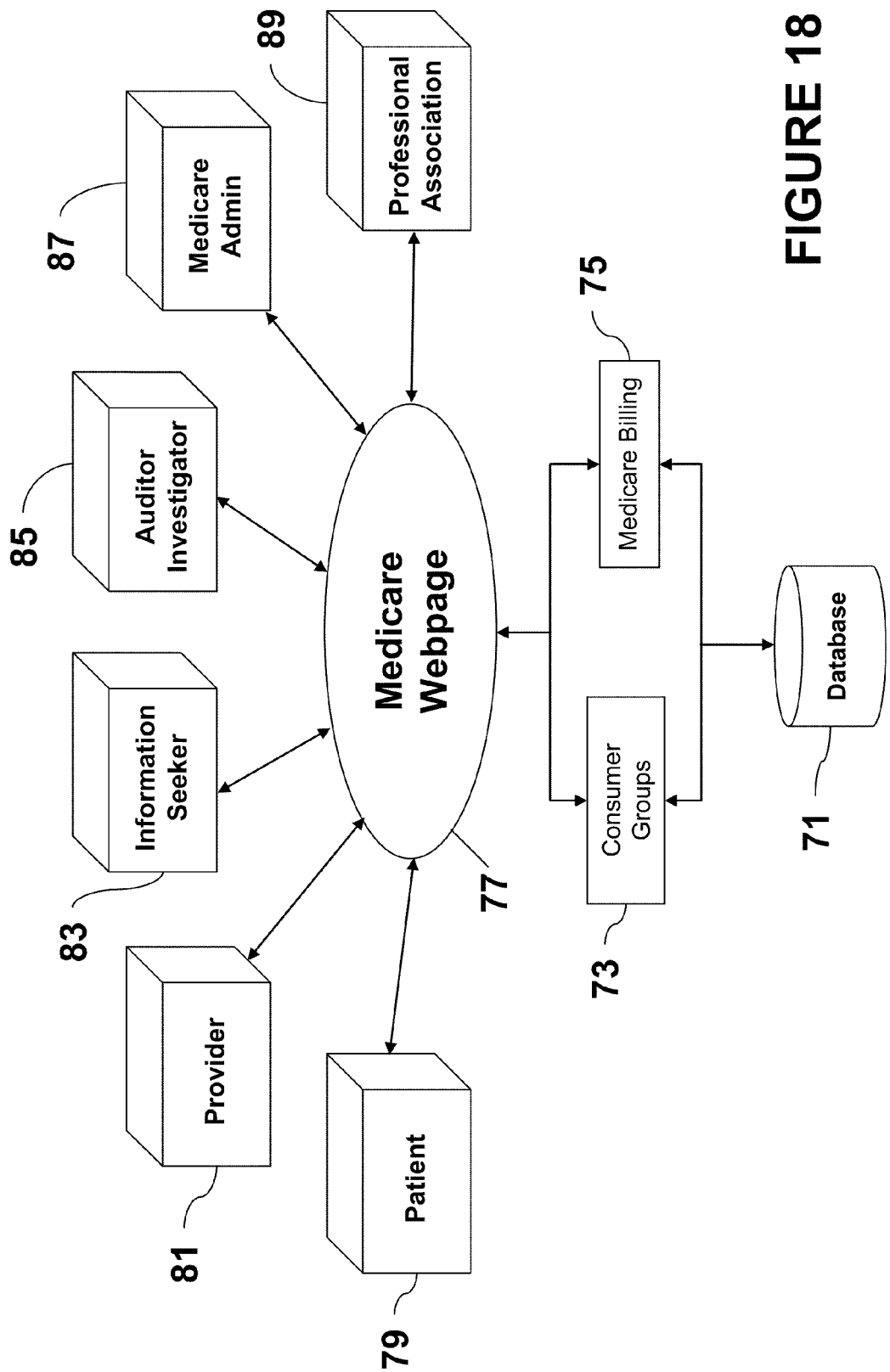
FIG. 18 is a diagram of an example patient-interactive healthcare management system as applied to Medicare.

FIG. 18 is an example illustration depicting patient-interactive healthcare management as applied to Medicare. The database comprises patient information collected via the information stations as described above. The database 71 can comprise for example, information pertaining to the quality of health care provided to patients, statistics pertaining to the accuracy of invoices, information pertaining to the overall quality of healthcare services provided, or the like. The information contained in the database 71 is available to Medicare billing 75. Medicare billing 75 can include any appropriate billing agency are entity responsible for handling billing matters for Medicare. In an example embodiment, the information contained in database 71 is available to consumer groups 73. Example consumer groups include e-Veritas, e-Orare, and e-Pacare. Information stored in a database 71 is available, via Medicare billing 75, to the Medicare webpage 77. Information on the Medicare webpage 77 is available to a variety of entities including, for example, the patient 79, a healthcare provider 81, any information seeker 84 having access to the Medicare webpage 77, an auditor investigator 85, the Medicare administrator 88, and a professional association 89.

Figure 19:
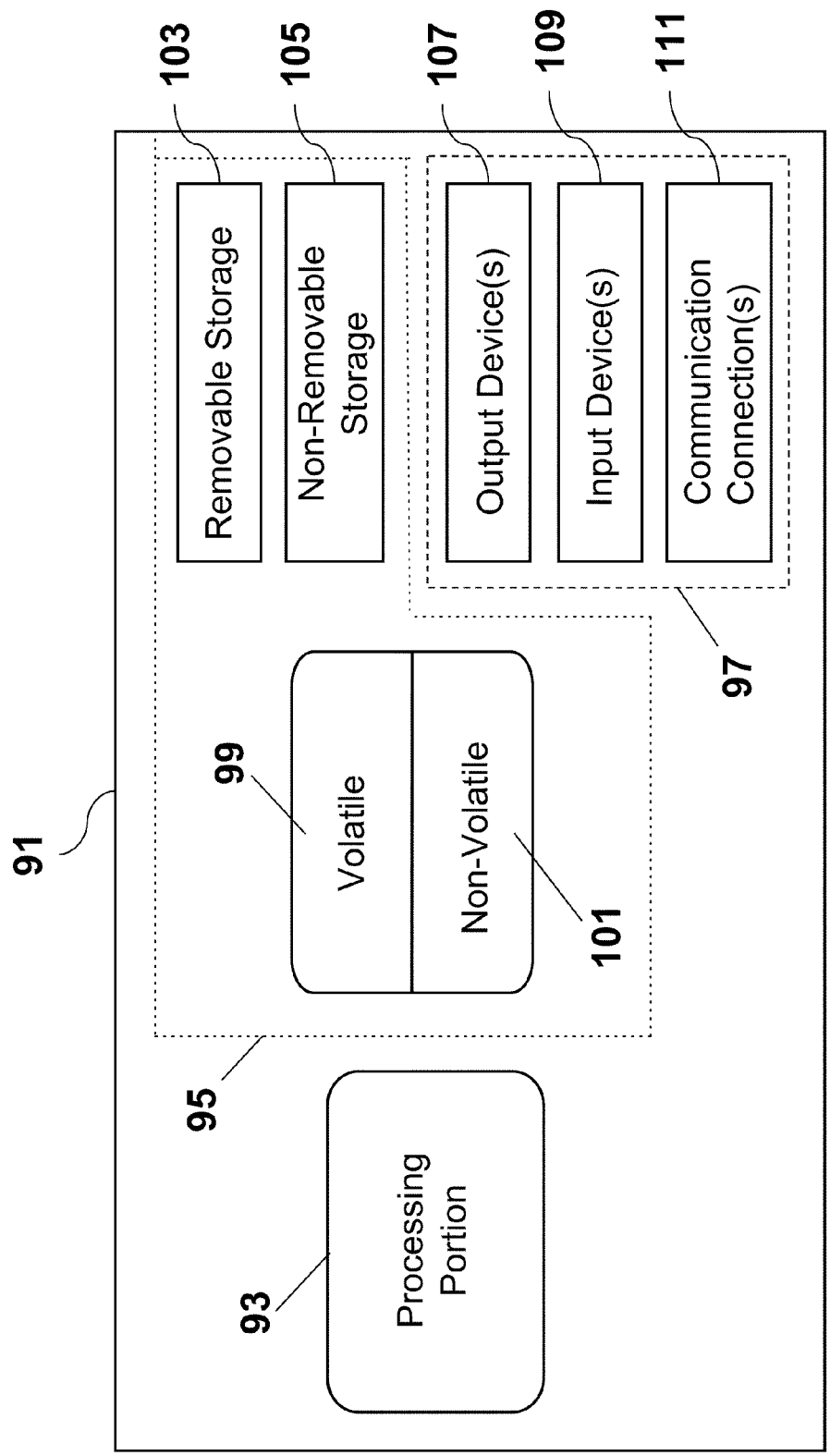
FIG. 19 is a diagram of an exemplary processor for implementing patient-interactive healthcare management.

The information station can comprise a processor or combination of processors. FIG. 19 is a diagram of an exemplary processor 91 for implementing patient-interactive healthcare management. The processor 91 comprises a processing portion 93, a memory portion 95, and an input/output portion 97. The processing portion 93, memory portion 95, and input/output portion 97 are coupled together (coupling not shown in FIG. 19) to allow communications therebetween. The input/output portion 97 is capable of providing and/or receiving components utilized to perform patient-interactive healthcare management as described above. For example, the input/output portion 97 is capable of, as described above, providing/receiving patient information, healthcare provider information, invoice verification information, information pertaining to the patient's assessment of the quality of healthcare services/goods provided, healthcare generic information, information pertaining to patient specific healthcare issues, encrypted information, or a combination thereof.

The processing portion 93 is capable of implementing patient-interactive healthcare management as described above. For example, the processing portion 93 is capable of calculating statistics based on provided patient healthcare information, determining trends based on provided patient healthcare information, or a combination thereof.

The processor 91 can be implemented as a client processor and/or a server processor. In a basic configuration, the processor 91 can include at least one processing portion 93 and memory portion 95. The memory portion 95 can store any information utilized in conjunction with patient-interactive healthcare management. For example, the memory portion 95 is capable of functioning as a repository for storing information for tracking durable medical equipment, prescribed medications, or the like. The memory portion 95 is capable of storing information pertaining to a practitioner profile, a patient profile, or a combination thereof, for example. Depending upon the exact configuration and type of processor, the memory portion 95 can be volatile (such as RAM) 99, non-volatile (such as ROM, flash memory, etc.) 101, or a combination thereof. The processor 91 can have additional features/functionality. For example, the processor 91 can include additional storage (removable storage 103 and/or non-removable storage 105) including, but not limited to, magnetic or optical disks, tape, flash, smart cards or a combination thereof. Computer storage media, such as memory portion 95, 99, 101, 103, and 105, include volatile and non-volatile, removable and non-removable media implemented in any method or technology for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, universal serial bus (USB) compatible memory, smart cards, or any other medium which can be used to store the desired information and which can be accessed by the processor 91. Any such computer storage media can be part of the processor 91.

The processor 91 can also contain communications connection(s) 111 that allow the processor 91 to communicate with other devices, such as other devices, for example. Communications connection(s) 111 is an example of communication media. Communication media typically embody computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. The term computer readable media as used herein includes both storage media and communication media. The processor 91 also can have input device(s) 109 such as keyboard, mouse, pen, voice input device, touch input device, a touch screen, a smart card, a patient identification card, or the like. Output device(s) 107 such as a display, speakers, printer, or the like also can be included.

While example embodiments of patient-interactive healthcare management have been described in connection with various computing devices, the underlying concepts can be applied to any computing device or system capable of implementing patient-interactive healthcare management. The various techniques described herein can be implemented in connection with hardware or software or, where appropriate, with a combination of both. Thus, the methods and apparatus for patient-interactive healthcare management, or certain aspects or portions thereof, can take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for implementing patient-interactive healthcare management. In the case of program code execution on programmable computers, the computing device will generally include a processor, a storage medium readable by the processor (including volatile and non-volatile memory and/or storage elements), at least one input device, and at least one output device. The program(s) can be implemented in assembly or machine language, if desired. In any case, the language can be a compiled or interpreted language, and combined with hardware implementations.

The methods and apparatus for patient-interactive healthcare management also can be practiced via communications embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, or the like, the machine becomes an apparatus for patient-interactive healthcare management. When implemented on a general-purpose processor, the program code combines with the processor to provide a unique apparatus that operates to invoke the functionality of patient-interactive healthcare management. Additionally, any storage techniques used in connection with patient-interactive healthcare management can invariably be a combination of hardware and software.

While patient-interactive healthcare management has been described in connection with the various embodiments of the various figures, it is to be understood that other similar embodiments can be used or modifications and additions can be made to the described embodiment for performing the same function of patient-interactive healthcare management without deviating therefrom. For example, one skilled in the art will recognize that a system for patient-interactive healthcare management as described may apply to any environment, whether wired or wireless, and may be applied to any number of devices connected via a network and interacting across the network. Therefore, patient-interactive healthcare management should not be limited to any single embodiment, but rather should be construed in breadth and scope in accordance with the appended claims.

What is claimed is:

1. A method comprising:
  responsive to receiving healthcare:
    selecting, by a patient that received the healthcare, via a processor, a treatment provided during the healthcare;
    providing treatment specific questions based on the selected treatment;
    evaluating, by the patient, the selected treatment by answering the treatment specific questions, via the processor, directed to treatment specific procedures performed during the received healthcare, wherein:
the evaluating is conducted at a location at which the patient was located during the received healthcare;
the evaluating occurs prior to notification to a third party pertaining to the received healthcare; and
providing, via the processor, information pertaining to the evaluation to a consumer profile.

2. The method of claim 1, wherein the consumer profile is indicative of patient satisfaction with the received healthcare.

3. The method of claim 1, wherein the consumer profile is utilizable to derive a healthcare report for the patient.

4. The method of claim 1, wherein the consumer profile is utilizable to derive a healthcare report for the patient obtained over a period of time.

5. The method of claim 1, wherein the consumer profile is utilizable to determine statistics pertaining to a healthcare-related issue.

6. The method of claim 1, wherein the consumer profile is utilizable to determine a risk factor of the patient pertaining to a chronic disease.

7. The method of claim 1, wherein the consumer profile is utilizable to determine if a weight of the patient is within an acceptable range.

8. The method of claim 1, wherein the consumer profile is utilizable to determine if a blood pressure of the patient is within an acceptable range.

9. The method of claim 1, wherein the consumer profile is utilizable to determine if the patient is at risk of an ailment.

10. The method of claim 1, wherein the consumer profile is utilizable to determine if the patient is at risk of at least on of diabetes, heart attack, stroke, kidney failure, or a foot aliment.

11. The method of claim 1, wherein the consumer profile is utilizable to derive a disease management profile.

12. A system comprising:
a processor; and
memory coupled to the processor, the memory comprising instructions that when executed by the processor cause the processor to effectuate operations comprising:
selecting, by a patient that received healthcare, a treatment provided during the healthcare;
evaluating, by the patient, the selected treatment by answering treatment specific questions directed to treatment specific procedures performed during the received healthcare, wherein:
the evaluation is conducted at a point of service, at which the patient was located during the received healthcare; and
the evaluation occurs prior to notification to a third party pertaining to the received healthcare; and
a computer readable storage medium comprising an indication of a result of the evaluation.

13. The system of claim 12, wherein the result of the evaluation comprises a verification of an accuracy of a cost of the healthcare service.

14. The system of claim 12, wherein the result of the evaluation comprises healthcare related information for tracking at least one of:
medical equipment; or
a medication.

15. The system of claim 12, wherein the result of the evaluation comprises an assessment of procedures performed by a practitioner in rendering the healthcare service.

16. The system of claim 12, wherein:
the evaluation comprises responding to a survey pertaining to the received healthcare; and
the result of the evaluation comprises a response to the survey.

17. A computer readable storage medium that is not a transitory propagating signal, the computer readable storage medium having stored thereon instructions for causing a processor to facilitate:
responsive to receiving healthcare:
selecting, by a patient that received the healthcare, a treatment provided during the healthcare;
providing treatment specific questions based on the selected treatment;
evaluating, by the patient, the selected treatment by answering the treatment specific questions directed to treatment specific procedures performed during the received healthcare, wherein:
the evaluating is conducted at a point of service, at which the patient was located during the received healthcare; and
the evaluating occurs prior to notification to a third party pertaining to the received healthcare; and
providing an indication of a result of the evaluating.

18. The computer readable storage medium of claim 17, the instructions further for causing the processor to facilitate verifying an accuracy of a cost of the healthcare service.

19. The computer readable storage medium of claim 18, the instructions further for causing the processor to facilitate:
upon a determination that the cost is accurate, providing an indication of the cost to an entity for paying at least a portion of the cost; and
upon a determination that the cost is inaccurate, correcting the inaccuracy.

20. The computer readable storage medium of claim 17, the instructions further for causing the processor to facilitate storing healthcare related information for tracking at least one of:
medical equipment; or
a medication.

21. The computer readable storage medium of claim 17, the instructions further for causing the processor to facilitate providing at least one of:
an indication of a rating of a healthcare provider; or
an indication of a patient specific healthcare report.

22. The computer readable storage medium of claim 17, wherein the evaluating comprises assessing procedures performed by a practitioner in rendering the healthcare service.

23. The computer readable storage medium of claim 17, the instructions further for causing the processor to facilitate responding to a survey pertaining to the received healthcare, wherein the result of the evaluation comprises a response to the survey.

24. The computer readable storage medium of claim 17, the instructions further for causing the processor to facilitate providing a result of the evaluation to an entity for paying at least a portion of a cost of the healthcare service.

25. The computer readable storage medium of claim 17, the instructions further for causing the processor to facilitate providing a result of the evaluation to a healthcare provider in order to change a healthcare related behavior.

26. The computer readable storage medium of claim 17, the instructions further for causing the processor to facilitate conducting a therapeutic intervention with the patient.

* * * * *